United States Patent [19]

Garnaud et al.

[11] 4,388,823
[45] Jun. 21, 1983

[54] APPARATUS FOR AUTOMATICALLY MEASURING THE VISCOSITY OF LIQUIDS

[75] Inventors: Guy Garnaud; Roger Bouhier, both of Poitiers, France

[73] Assignee: Medica-Test, Saint-Benoit, France

[21] Appl. No.: 242,387

[22] Filed: Mar. 10, 1981

[30] Foreign Application Priority Data

Mar. 26, 1980 [FR] France ............................ 80 06658

[51] Int. Cl.³ ............................................ G01N 11/12
[52] U.S. Cl. .................................................... 73/57
[58] Field of Search ............................................. 73/57

[56] References Cited

U.S. PATENT DOCUMENTS

| | | |
|---|---|---|
| 2,252,572 | 8/1941 | Lang . |
| 2,320,218 | 5/1943 | Buckley . |
| 2,778,220 | 1/1957 | Kuhlmann et al. .............. 73/57 |
| 2,957,338 | 10/1960 | Kennedy et al. .............. 73/57 |
| 3,368,391 | 2/1968 | Harrison . |
| 3,677,070 | 7/1972 | Norcross ........................ 73/57 |
| 3,967,934 | 7/1976 | Seitz et al. ..................... 73/57 X |

FOREIGN PATENT DOCUMENTS

1491865 11/1977 United Kingdom .
635410 11/1978 U.S.S.R. ........................ 73/57

OTHER PUBLICATIONS

A Viscometer with Magnetic Lift, by N. V. Belonenko, in Industrial Lab., vol. 41, No. 1, pp. 64, 92, Jan. 1975 translation from U.S.S.R., Jul. 1975.
"Soviet Journal of Instrumentation and Control", No. 6, Jun. 1969, An Automatic Sphere Viscometer, by A. N. Melekhin and N. K. Chertkou.
Review of Scientific Instruments, vol. 48, No. 7, Jul. 1977, "Small-Volume, Inclined, Falling-Ball Viscometer", by R. H. Geils and R. C. Keezer.

*Primary Examiner*—Anthony V. Ciarlante
*Assistant Examiner*—David U. Carlson
*Attorney, Agent, or Firm*—Young & Thompson

[57] ABSTRACT

The apparatus for measuring the viscosity of liquids comprises an inclined viscosimetric tube (1) enclosing a ball (3). A device is provided for measuring the duration of fall of the ball (3) in the tube (1). An electromagnet (8) adjacent the tube (1) has poles (9) which set up along the tube (1) a gradient of a magnetic field allowing the automatic rising of the ball (3). The apparatus is used mainly for measuring the viscosity and the time of the coagulation of blood.

4 Claims, 4 Drawing Figures

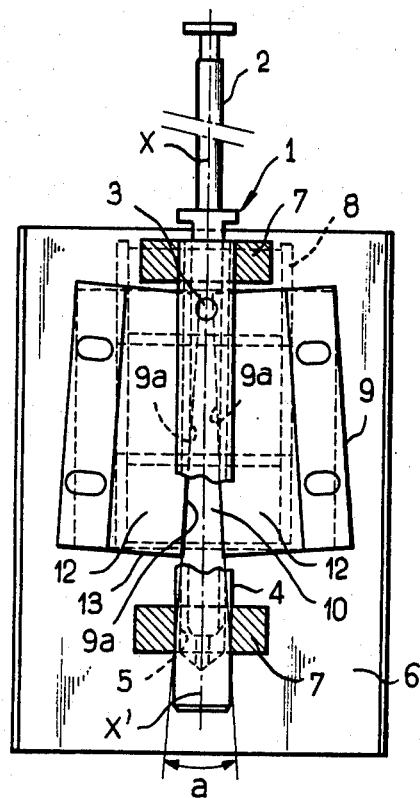
FIG_1
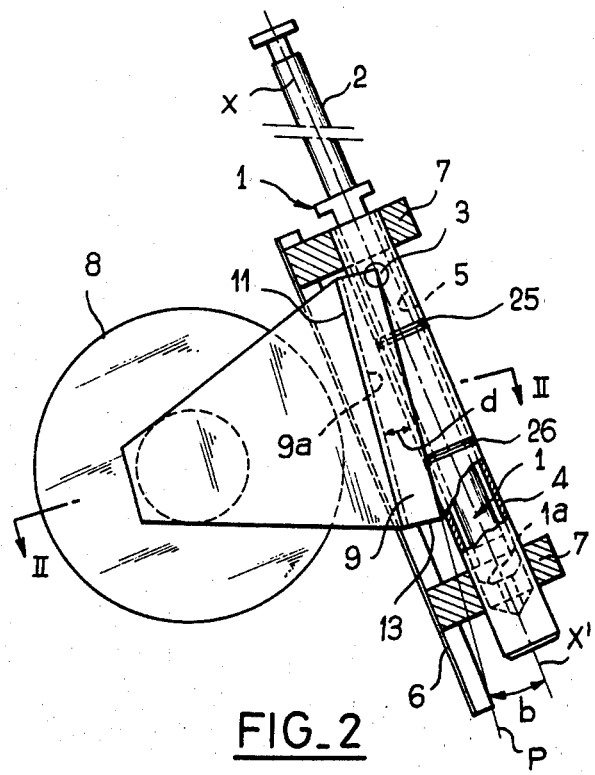
FIG_2

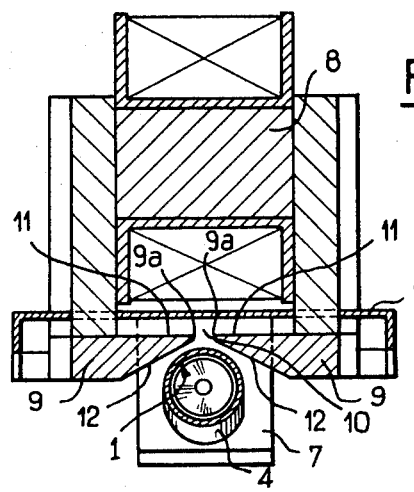
FIG_3
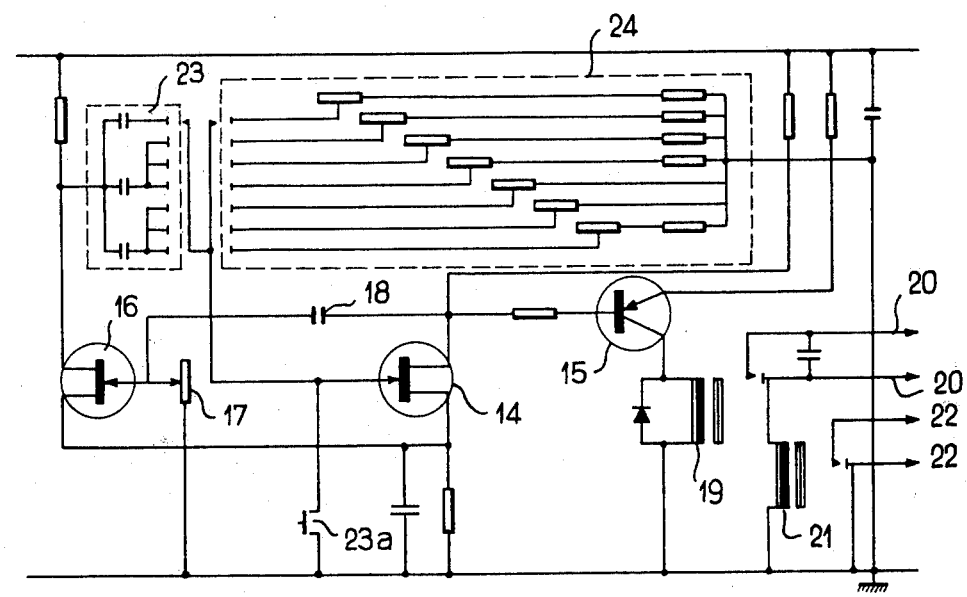
FIG_4

APPARATUS FOR AUTOMATICALLY MEASURING THE VISCOSITY OF LIQUIDS

The present application relates to an apparatus for automatically measuring the viscosity of liquids.

This apparatus is primarily intended for measuring the viscosity of blood, but can also be used for other liquids, the viscosity of which is of interest, such as hydrocarbons, paints, varnishes, inks, syrupy liquids and the like.

In the medical field, the measuring of the viscosity of blood and especially the evolution thereof up to coagulation, yields very interesting information on certain diseases.

Already known are viscosimeters having a viscosimetric tube, kept in substantially vertical position and surrounding a small ball, means for introducing the liquid to be tested in the tube and for measuring the duration of fall of said ball in the tube containing the liquid. This measuring of the duration of fall allows the determination of the viscosity by different means, well known to those skilled in the art.

After having measured said duration of the fall, the small ball must be placed back in its original position. This operation is generally carried out manually by reversing the viscosimetric tube.

Such known devices have the drawbacks of not being very reliable, somewhat awkward in use and causing difficulties in making exact and repetitive measurements which are indispensable for cases where the evolution of the viscosity of a liquid is to be studied during a certain length of time. The properties of viscosity and coagulation of blood depend on the shearing stress to which the blood is submitted prior to measuring, i.e. the manner in which the blood is agitated or stirred up. The result is that the measurements must preferably be made in the sample-taking syringe directly after taking the samples at intervals of time known in homogenous and reproducible mixing. The rising of the ball in the viscosimeter causes a mixing of the blood and, as a result thereof, the ball must rise through the entire column of liquid, failing which, in the upper part groups of red corpuscules gather in packets, with clots forming uncontrollably and causing successive false measurements.

Homogenous mixing which need not be too strong so as to avoid the alteration of the mechanical properties of the blood, can only be effective if the ball rises relatively slowly and with regularity. The result is that said rising of the ball cannot be caused by the action of an electromagnet or a regular solenoid on a magnetic ball. In particular, in a solenoid the longitudinal field component is either constant (except at its ends) in a long solenoid and the ball cannot move an appreciable distance, or the zone of rising is very short in a short solenoid in which said field is nowhere constant. Also, the speed of rising of the ball is very fast if no special device is used for causing a convenient gradient.

Thus the known devices are not suitable for measuring accurately, for example, the viscosity of blood, considering, on the one hand, the speed with which said viscosity evolves during a period of time on account of the coagulation and, on the other hand, on account of the need to create under all conditions a homogenous mixing.

The object of the present invention is to provide an apparatus for measuring the viscosity of liquids which is at the same time very precise, easy to use and which allows repeated measurements in close intervals of time, with homogenous mixing and which, for this reason, is especially well adapted for measuring the viscosity of a liquid like blood where the viscosity evolves very rapidly.

The apparatus according to the invention comprises a viscosimetric tube which is in an inclined position and encloses a ball, means for introducing the liquid to be tested into said tube and means for measuring the duration of the fall of said ball in the tube containing the liquid, said means being associated with means for converting the duration of fall of the ball into viscosity, and electromagnetic means allowing to raise the ball of magnetic material to the top of the tube and to hold it in this high position, and means for suppressing the magnetic field to allow the ball to fall in the tube.

According to the invention, this apparatus is characterized in that said electromagnetic means comprise means for applying along the tube with the ball of magnetic material a magnetic field gradient which is directed toward the top of the tube.

The preceding means are preferably in the form of an electromagnet placed along the entire useful height of the viscosimetric tube.

Thus, at the end of measuring, it is sufficient to energize the electro-magnet for raising the ball. This rise is assured by the magnetic field gradient created along the tube. The ball stops at the top of the tube at a precise place, perfectly reproducible, where the magnetic field is most intense. For taking a measurement it is sufficient to cut the input of electric current to the electro-magnet, whereby the fall of the ball is caused. The rise and the fall of the ball thus take place automatically without having to move any part of the apparatus. This allows taking successive measurements in very short intervals, so that it is possible to follow under the excellent conditions the viscosity and coagulation of a liquid such as blood.

According to an advantageous embodiment of the invention, the electro-magnet comprises two poles representing ends which are fixed with respect to one another and define an elongated and narrow air gap along which the viscosimetric tube is placed, whereby the distance between the tube and the ends of the two poles increases progressively between the top and the base of the tube.

Thus the magnetic field is augmented progressively between the base and the top of the tube. In this manner the ball is automatically attracted, and that at a regular speed, from the base of the tube toward the point positioned in the upper part of the tube where the magnetic field is most intense.

According to a preferred embodiment of the invention, the apparatus comprises a fixed support of nonmagnetic material, and the viscosimetric tube may be in the form of a disposable syringe intended to be removably positioned in said tube support.

Said syringe thus also plays at the same time the role of a liquid sample-taking element for testing and a viscosimetric tube. In the case where the liquid is blood and where it is desired to carry out successive measurements in short intervals of time, it is advantageous to provide a series of disposable syringes.

In such a case it is also of advantage to associate the electro-magnet with control means which allow automatic and periodic operation of this electro-magnet so that repeated measurements can be carried out.

Other features and advantages will be set forth in the following description.

The attached drawings give non-limitative examples:

FIG. 1 is an elevation with pulled-up portions in front of an apparatus according to the invention.

FIG. 2 is a side elevation of the apparatus according to FIG. 1.

FIG. 3 is a sectional view along the line II—II of FIG. 2.

FIG. 4 is a schematic view of the electronic control circuit for the operation of the electro-magnet.

In the embodiments of FIGS. 1 and 2 the apparatus according to the invention comprises a syringe 1 having a piston 2 and enclosing a liquid, the viscosity of which is to be measured. Said syringe 1 encloses a small ball of magnetic material such as ordinary stainless steel which may have a protective cover to avoid any chemical effects thereon by the liquid to be tested. The syringe 1 is preferably disposable, especially when the liquid to be tested is hard to wash out.

The syringe 1 is removably arranged in the inner hollow space 5 of a tubular support 4 of plastic material. This tubular support 4 is fixed against a plate 6 by means of two arms 7. Said plate is attached to a stand, not shown, which assures the stability of the apparatus.

In the back of the plate 6 an electro-magnet 8 is provided which is solidly fixed to the stand of the apparatus. Said electro-magnet comprises two poles 9 whose ends 9a are positioned relative to each other (see FIG. 3). These ends 9a define a lengthened and narrow air gap 10 along which the tubular support 4 is placed in which the syringe 1 is arranged.

FIG. 2 shows clearly that the distance d between the tubular support 4 and the ends 9a of the poles 9 increase progressively between the top and the base of the support 4. In the interior of the syringe 1 a gradient of a magnetic field produces a force directed toward the top of the syringe 1.

In the example shown the poles 9 have near their ends 9a a transverse triangular section. The surfaces 11 of the poles 9 positioned opposite the tubular support 4 are arranged in the prolongation of the one relative to the other. The surfaces 12 of said poles 9 adjacent the tubular support 4 define a dihedral, inside of which said support 4 is arranged.

The ends 9a of the poles 9 are rectilinear and form between them an angle a (FIG. 1). This angle a can vary between 0° and 20°.

At the upper portion of the tubular support 4, the ends 9a of the poles 9 are positioned a few millimeters one from the other and from the outer wall of the tubular support 4. This distance is noticeably smaller than the diameter of the syringe 1. At this location the magnetic field produced by the electro-magnet 8 is most intense.

The axis X—X' of the syringe 1 forms with the plane P, which is parallel to the surface 11 of the poles 9, an angle b which can vary between about 5° and 20°.

In the position shown in FIGS. 1 and 2, the electro-magnet 8 is energized and the ball 3 is kept at the upper part of the syringe 1, close to the piston 2 of the latter, at the location where the magnetic field is most intense. When the electric current to the electro-magnet is interrupted, the fall of the ball 3 toward the lower end of the syringe 1 is triggered.

The lower edge 13 of the poles 9 is at a distance sufficiently reduced from the lower end 1a of the syringe so that the magnetic field can lift up the ball from said end 1a.

The device for automatically raising the ball 3 makes it possible to carry out repetitive measurements of viscosity according to a cycle which functions completely automatically.

The electro-magnet 8 is associated for said purpose with a control circuit for the automatic operation as is shown in FIG. 4.

This electronic circuit comprises a first temporization circuit which determines the time of current passage in the electro-magnet 8. This first temporization circuit comprises in essence transistors with stray-field effect 14 and 16 which allow a sufficiently long constant of time, and a transistor amplifier 15. This circuit also comprises a resistor 17 and a capacitor 18, a relay 19 controlling the electric feed circuit 20 of the electro-magnet 8 and another relay 21 controlling the return to zero at 22 of an electronic chronometer not shown.

The manual starting of said first delaying circuit is carried out by a circuit-breaker 23a.

The functioning of said first temporization circuit is as follows:

When the circuit-breaker 23a is closed, the transistor 14 is made conductive for a time sufficiently long to allow the transistor 15 to become conductive and close the relay 19. The latter closes the electric supply circuit 20 of the electro-magnet 8 and puts the electronic chronometer which is connected with the circuit 22 by the relay 21, back to zero.

At the end of a period defined by the time constant due to 17 and 18, the transistor 16 becomes a conductor, the transistors 14 and 16 block themselves which causes interrupting the feed circuit 20 of the electro-magnet 8 and the falling of the ball 3. It is now possible to measure the duration of fall of the ball, as explained below.

The second variable temporization circuit is defined by the electric circuits 23 and 24. This variable temporization circuit modifies the cadence of reproducing the measuring cycle according to the variable periods which are, for example, equal to 5, 10, 20 and 40 seconds.

The means for automatically measuring the time of fall of the ball 3 comprise (see FIG. 2) two induction coils 25, 26 which axially surround the tubular support 4 and are, for example, spaced from one another by 20 mm. The two coils 25, 26 set up self-inductions of an oscillating circuit whose variations of frequency due to the passage of the ball are detected and transferred into impulses capable of controlling an electronic chronometer or an internal clock of a microprocessor.

Experience has shown that the apparatus according to the invention allows to attain extremely accurate measurements of viscosity which are also perfectly reproducible for the same liquid. Thus, in the case of the example shown, the durations of the falling of the ball at a constant temperature were constant to 1/1000.

It is to be noted that the invention is not limited to the described example but that many modifications are possible within the scope of the invention.

Thus, to carry out measurements of the viscosity of blood under conditions of weak shearing, i.e. upon slow movement of the ball, the device according to FIG. 2 comprising the electro-magnet and the viscosimetric tube can be carried by a support whose inclination is adjustable and which has two predetermined extreme positions of such type as to allow the inclination of the viscosimetric tube to be changed relative to the vertical direction.

The electro-magnet 8 can be replaced by or combined with a solenoid which is coaxial with the viscosimetric tube and has a plurality of spires per unit of length which is greater at the upper part of the tube than at its lower part and/or a diameter of the spires which is smaller, so as to create an appropriate gradient of the magnetic field.

In order to increase the efficiency of the solenoid (by reducing the resistance of the magnetic circuit outside the solenoid), it may be advisable to conduct the outer lines of the field by iron. The electric circuit of iron can be a cylinder, coaxial with the solenoid, surrounding it at the outside. It can include a pole piece at its upper portion (with the two poles of the solenoid at the two ends, it occurs that the local intensity of the field is not augmented by a pole piece at the lower portion). This pole piece can be a ring surrounding the support of the syringe and capable of stabilizing the ball in a precise position which should be substantially in the center of said ring.

In another modification the passing of the ball 3 through a single induction coil leads to a variation in frequency causing a variation in voltage, the slope of which is proportionate to the speed of the fall. Said voltage shown on the numeric voltmeter can be transformed into a viscosity value by calculation.

The apparatus according to the invention can be used for measuring with extreme accuracy the time of coagulation of blood.

Measuring the time of coagulation is carried out by a chronometer, the start of which is triggered by a pulse due at the passage of the ball 3 through the induction coil 25, i.e. from the introduction of the syringe 1 into the apparatus. The stopping of the chronometer is caused as soon as the ball 3 ceases to move and to give pulses to the measuring system.

For practical needs the apparatus according to the invention can be provided with the following accessories: thermo-regulated enclosure surrounding the support 4 of the syringe 1, electronic thermometer taking the temperature close to the syringe 1, chronometer measuring the duration of the coagulation and recording means for the times of fall, the viscosity, the temperature and the duration of coagulation.

The apparatus according to the invention is further advantageously supported by three leveling screws and can include a bubble-level to allow its correct horizontal positioning.

Besides, the apparatus according to the invention may include an additional induction coil arranged at the upper portion of the viscosimetric tube or the syringe 1 for blocking, in closed position the control relay 19 for energizing the electro-magnet 8 as long as the ball 3 is not in its upper position.

The apparatus according to the invention can be utilized for measuring the viscosity of all liquids such as hydrocarbons, oil, paint, varnish, ink, biological liquids, salt solutions, syrupy solutions, and suspensions. It can be used in all cases where it is useful to know the viscosity, in particular in the chemical industry for regulating the power of liquid pumps. In the paint industry it allows the addition of the right amount of solvents to paints and varnishes. In the medical field it is utilized for controlling those diseases which have an impact on the viscosity or the coagulation of the blood and for controlling the risks of operations relative to the viscosity. In the pharmaceutical field the apparatus according to the invention can help in controlling the reaction of medicines on the viscosity of the blood. In the food industry the improved apparatus serves for controlling syrups and the operation of gelling. It can also make fast measurements of the state of saturation of solutions.

We claim:

1. Apparatus for automatically measuring the viscosity of liquids, comprising in combination a viscosimetric tube (1), kept in an inclined position and containing a ball (3) made of magnetic material, means (2) for introducing the liquid to be tested in said tube and means for measuring the duration of fall of said ball (3) in the tube (1) containing the liquid, said means being associated with means for converting into viscosity the duration of fall of the ball (3) from the top of the tube, electromagnetic means for applying to said ball a magnetic field so as to maintain said ball at the top of said tube and means for suppressing the magnetic field and allowing the fall of the ball (3) in the tube (1), wherein said electromagnetic means (8) comprise an electromagnet having two poles with their ends (9a) being disposed relative to one another and defining an air gap (10) which is lengthy and narrow, along which the viscosimetric tube (1) is placed, with the distance (d) between said tube and the ends (9a) of the two poles (9) augmenting progressively between the top and the bottom of the tube (1), so as to create along the tube a magnetic field gradient directed towards the top of the tube which permits automatic rising of the ball from the bottom of the tube to the top of the tube when the electromagnet is energized.

2. Apparatus according to claim 1, wherein said electromagnet (8) is associated with control means (14 to 24) allowing automatic and periodic operation of the electromagnet for the purpose of performing repetitive measurements of viscosity, and wherein said control means comprise a first temporization circuit (23, 24) controlling the stopping of operation of the electromagnet (8) during a controllable and adequate period for allowing the measurement of the duration of fall of the ball (3), and a second temporization circuit (14 to 18) which controls by means of a relay (19) the energizing of the electromagnet (8) during an adequate period for allowing the rising of the ball in the viscosimetric tube (1).

3. Apparatus according to claim 1 wherein said poles (9) have near their ends (9a) a transverse, triangular section, with the ends (9a) of said poles being rectilinear and forming between them an angle (a) substantially between 0° and 20°, the minimal distance between the ends (9a) being smaller than the diameter of the tube (1) and the latter forming with a plane (P) parallel to the two rectilinear ends (9a) of the poles (9) an angle (b) between 5° and 20°.

4. Apparatus according to claim 3, wherein said air gap (10) defined between the poles (9) of the electromagnet (8) has a length which is substantially equal to the height of the fall of the ball (3).

* * * * *